(12) United States Patent
DeWolf, Jr. et al.

(10) Patent No.: US 6,821,746 B2
(45) Date of Patent: Nov. 23, 2004

(54) METHODS OF SCREENING FOR FABK ANTAGONISTS AND AGONISTS

(75) Inventors: Walter E. DeWolf, Jr., Collegeville, PA (US); David John Payne, Collegeville, PA (US); Nicola Gail Wallis, Cambridge (GB); Joshua M. West, Collegeville, PA (US)

(73) Assignee: Affinium Pharmaceuticals, Inc., Ontario (CA)

( * ) Notice: Subject to any disclaimer, the term of this patent is extended or adjusted under 35 U.S.C. 154(b) by 0 days.

(21) Appl. No.: 09/968,129

(22) Filed: Oct. 1, 2001

(65) Prior Publication Data

US 2004/0137548 A1 Jul. 15, 2004

Related U.S. Application Data

(60) Provisional application No. 60/238,366, filed on Oct. 6, 2000.

(51) Int. Cl.$^7$ ............................ C12Q 1/32; G01N 33/53
(52) U.S. Cl. ........................................ 435/26; 435/7.1
(58) Field of Search .................................... 435/26, 7.1

(56) References Cited

U.S. PATENT DOCUMENTS 6,613,553 B1   9/2003   Rock et al.

FOREIGN PATENT DOCUMENTS

| EP | 826774 A2 * | 3/1998 | ........... C12N/15/53 |
|----|----|----|----|
| WO | WO 98/06734 | 2/1998 | |
| WO | WO 98/18931 | 5/1998 | |
| WO | WO 98/26072 | 6/1998 | |
| WO | WO 01/30988 | 5/2001 | |
| WO | WO 01/49721 | 7/2001 | |
| WO | WO 01/70995 | 9/2001 | |
| WO | WO 0231128 A1 * | 4/2002 | ............ C12N/9/00 |

OTHER PUBLICATIONS

Anon., "Triclosan–resistant Enzyme" (Jul. 17, 2000) Chemical & Engineering News, vol. 78, No. 29, pp. 39.*
Bhargava, et al., "Triclosan: Applications and safety", *American Journal of Infection Control*, 24: 209–218 (1996).
Rock, et al., "Preparative Enzymatic Synthesis and Hydrophobic Chromatography of Acyl–Acyl Carrier Protein", *The Journal of Biological Chemistry*, 254(16): 7123–7128 (1979).
Rock, et al., "Lipid metabolism in prokaryotes", *Biochemistry of Lipids, Lipoproteins and Membranes*, Elsevier Publishing Company Amsterdam, 35–74 (1996).
Rock, et al., "*Escherichia coli* as a model for the regulation of dissociable (type II) fatty acid biosynthesis", *Biochimica et Biophysica Acta*, 1302: 1–16 (1996).
Heath, et al., "Mechanism of Triclosan Inhibition of Bacterial Fatty Acid Synthesis", *The Journal of Biological Chemistry*, 274(16): 11110–11114 (1999).
Gadda, et al., "Substrate Specificity of a Nitroalkane–Oxidizing Enzyme", *Archives of Biochemistry and Biophysics*, 363(2): 309–313 (1999).
McMurray, et al., "Triclosan targets lipid synthesis", *Nature*, 394: 531–532 (1998).
Ross, et al., "Molecular Cloning and Analysis of the Gene Encoding the NADH Oxidase from *Streptococcus faecalis* 10C1", *Journal of Molecular Biology*, 227: 658–671 (1992).
Marion Bradford, A Rapid and Sensitive Method for the Quantitation of Microgram Quantities of Protein Utilizing the Principle of Protein–Dye Binding, *Analytical Biochemistry*, 72: 248–254 (1976).
Tchorzewski, et al., "Unique primary structure of 2–nitropropane dioxygenase from Hansenula mrakii", *European Journal of Biochemistry*, 226: 841–846 (1994).
Komuniecki, et al., "Electron–transfer flavoprotein from anaerobic *Ascaris suum* mitochondria and its role in NADH–dependent 2–methyl branched–chain enoyl–CoA reduction", *Biochimica et Biophysica Acta*, 975: 127–131 (1989).
Baker, et al., "Enoyl–acyl–carrier–protein reductase and *Mycobacterium tuberculosis* InhA do not conserve the Tyr–Xaa–Xaa–Xaa–Lys motif in mammalian 11β–and 17β–hydroxysteroid dehydrogenases and *Drosophila* alcohol dehydrogenase", *Biochemical Journal*, 309: 1029–1030 (1995).
Gibson, et al., "Contribution of NADH Oxidase to Aerobic Metabolism of *Streptococcus pyogenes*", *Journal of Bacteriology* 182(2): 448–455 (2000).
Boynton, et al., "Cloning, Sequencing, and Expression of Clustered Genes Encoding β–Hydroxybutyryl–Coenzyme A (CoA) Dehydrogenase, Crotonase, and Butyryl–CoA Dehydrogenase from *Clostridium acetobutylicum* ATCC 824", *Journal of Bacteriology*, 178(11): 3015–3024 (1996).
Heasley, et al., "Kinetic Mechanism and Substrate Specificity of Nitroalkane Oxidase", *Biochemical and Biophysical Research Communication*, 225: 6–10 (1996).
Havarstein, et al., "An unmodified heptadecapeptide phenone induces competence for genetic transformation in *Streptococcus pneumoniae*", *Proceedings of the National Academy of Science USA*, 92: 11140–11144 (1995).
De–Gonzalez, et al., "NAD–Independent Lactate and Butyryl–CoA Dehydrogenases of *Clostridium acetobutylicum* P262", *Current Microbiology*, 34: 162–166 (1997).
Slater–Radosti, et al., "Biochemical and genetic characterization of the action of triclosan on *Staphylococcus aureus*," *Journal of antimicrobial Chemotherapy*, 48: 1–6 (2001).
Heath, et al., "A triclosan–resistant bacterial enzyme", *Nature*, 406: 145–146 (2000).
Heath, et al., "Broad Spectrum Antimicrobial Biocides Target the FabI Component of Fatty Acid Synthesis", *The Journal of Biological Chemistry*, 273(46): 30316–30320 (1998).

(List continued on next page.)

Primary Examiner—Jon P. Weber
(74) Attorney, Agent, or Firm—Foley Hoag, LLP

(57) ABSTRACT

The invention provides methods for identifying agonists and antagonists of FabK polypeptides.

12 Claims, No Drawings-

OTHER PUBLICATIONS

Saito, et al., "Genetic Evidence That Phosphatidylserine Synthase II Catalyzes the Conversion of Phosphatidylethanolamine to Phosphatidylserine in Chinese Hamster Ovary Cells", *The Journal of Biological Chemistry*, 273 (27): 17199–17205 (1998).

Roujeinikova, et al., "Inhibitor Binding Studies on Enoyl Reductase Reveal Conformational Changes Related to Substrate Recognition", *The Journal of Biological Chemistry*, 274(43): 30811–30817 (1999).

Bergler, et al., "Protein EnvM Is the NADH–dependent Enoyl–ACP Reductase (FabI) of *Escherichia coli*", *The Journal of Biological Chemistry*, 269(8): 5493–5496 (1996).

Duran, et al., "Characterization of cDNA Clones for the 2–Methyl Branched–chain Enoyl–CoA Reductase", *The Journal of Biological Chemistry*, 268(30): 22391–22396 (1993).

Volkman, et al., "Biosynthesis of D–Alanyl–Lipoteichoic Acid: The Tertiary Structure of apo–D–Alanyl Carrier Protein", *Biochemistry*, 40: 7964–7972 (2001).

Ward, et al., "Kinetic and Structural Characteristics of the Inhibition of Enoyl (Acyl Carrier Protein) Reductase by Triclosan", *Biochemistry*, 38: 12514–12525 (1999).

Parkh, et al., "Roles of Tyrosine 158 and Lysine 165 in the Catalytic Mechanism of InhA, the Enoyl–ACP Reductase from *Mycobacterium tuberculosis*", *Biochemistry*, 38: 13623–13634 (1999).

Roujeinikova, et al., "Crystallographic Analysis of Triclosan Bound to Enoyl Reductase", *Journal of Molecular Biology*, 294: 527–535 (1999).

Heath, et al., "Inhibition of the *Staphylococcus aureus* NADPH–dependent Enoyl–Acyl Carrier Protein Reductase by Triclosan and Hexachlorophene", *The Journal of Biological Chemistry*, 275(7): 4654–4659 (2000).

Heath, et al., "Inhibition of β–Ketoacyl–Acyl Carrier Protein Synthase III (FabH) by Acyl–Acyl Carrier Protein in *Escherichia coli*", *The Journal of Biological Chemistry*, 271(18): 10996–11000 (1996).

Heath, et al., "Roles of the FabA and FabZ β–Hydroxyacyl Carrier Protein Dehydrotases in *Escherichia coli* Fatty Acid Biosynthesis", *The Journal of Biological Chemistry*, 271(44): 27795–27801 (1996).

Heath, et al., "The Enoyl–[acyl–carrier–protein] Reductases FabI and FabL from *Bacillus subtilis*", *The Journal of Biological Chemistry*, 275(51): 40128–40133 (2000).

Heath, et al., "Regulation of Fatty Acid Elongation and Inititation by Acyl–Acyl Carrier Protein in *Escherichia coli*", *The Journal of Biological Chemistry*, 271(4): 1833–1836 (1996).

Bunzow, et al., "Cloning and expression of a rat $D_2$ dopamine receptor cDNA", *Nature*, 336: 783–787 (1988).

Whitfield, et al., "Purification and Properties of Electron–transferring Flavoprotein and *Peptostreptococcus elsdenii*", *The Journal of Biological Chemistry*, 249(9): 2801–2810 (1974).

Baldwin, et al., "Electron transport in *Peptostreptococcus elsdenii*", *Biochimica et Biophysica Acta*, 92: 421–432 (1964).

Heath, et al., "Enoyl–Acyl Carrier Protein Reductase (*fabI*) Plays a Determinant Role in Completing Cycles of Fatty Acid Elongation in *Escherichia coli*", *The Journal of Biological Chemistry*, 270(44): 26538–26542 (1995).

Egan, et al., "Conditional mutations affecting the cell envelope of *Escherichia coli* K–12", *Genetic Research*, 21: 139–152 (1973).

Marrakchi et al., Characterization of *Streptococcus pneumoniae* enoyl–(acyl–carrier protein) reductase (FabK), Biochem. J., 370:1055–1082 (2003).

* cited by examiner

SEQUENCE LISTING

<160> NUMBER OF SEQ ID NOS: 4

<210> SEQ ID NO 1
<211> LENGTH: 975
<212> TYPE: DNA
<213> ORGANISM: Streptococcus pneumoniae

<400> SEQUENCE: 1

```
atgaaaacgc gtattacaga attattgaag attgactatc ctattttcca aggagggatg      60
gcctgggttg ctgatggtga tttggcaggg gctgtttcca aggctggagg attaggaatt     120
atcggtgggg gaaatgcccc gaaagaagtt gtcaaggcca atattgataa aatcaaatca     180
ttgactgata aacccttttgg ggtcaacatc atgctcttat ctcccttttgt ggaagatatc     240 gtggatctcg ttattgaaga aggtgttaaa gttgtcacaa caggagcagg aaatccaagc     300
aagtatatgg aacgtttcca tgaagctggg ataatcgtta ttcctgttgt tcctagtgtc     360
gctttagcta aacgcatgga aaaaatcggt gcagacgctg ttattgcaga aggaatggaa     420 gctgggggc atatcggtaa attaacaacc atgaccttgg tgcgacaggt agccacagct     480
atatctattc ctgttattgc tgcaggagga attgcggatg gtgaaggtgc tgcggctggc     540
tttatgctag gtgcagaggc tgtacaggtg gggacacggt ttgtagttgc aaaagagtcg     600
aatgcccatc caaactacaa ggagaaaatt ttaaaagcaa gggatattga tactacgatt     660
tcagctcagc actttggtca tgctgttcgt gctattaaaa atcagttgac tagagatttt     720
gaactggctg aaaaagatgc ctttaagcag gaagatcctg atttagaaat ctttgaacaa     780
atgggagcag gtgccctagc caaagcagtt gttcacggtg atgtggatgg tggctctgtc     840
atggcaggtc aaatcgcagg gcttgtttct aaagaagaaa cagctgaaga aatcctaaaa     900
```

```
gatttgtatt acggagccgc taagaaaatt caagaagaag cctctcgctg ggcaggagtt      960
gtaagaaatg actaa                                                      975
```

```
<210> SEQ ID NO 2
<211> LENGTH: 324
<212> TYPE: PRT
<213> ORGANISM: Streptococcus pneumoniae

<400> SEQUENCE: 2
```

| | | | | | | | | | | | | | | |
|---|---|---|---|---|---|---|---|---|---|---|---|---|---|---|
| Met | Lys | Thr | Arg | Ile | Thr | Glu | Leu | Leu | Lys | Ile | Asp | Tyr | Pro | Ile | Phe |
| 1 | | | | 5 | | | | | 10 | | | | | 15 | |

Gln Gly Gly Met Ala Trp Val Ala Asp Gly Asp Leu Ala Gly Ala Val
            20                  25                  30

Ser Lys Ala Gly Gly Leu Gly Ile Ile Gly Gly Asn Ala Pro Lys
        35                  40                  45

Glu Val Val Lys Ala Asn Ile Asp Lys Ile Lys Ser Leu Thr Asp Lys
 50                  55                  60

Pro Phe Gly Val Asn Ile Met Leu Leu Ser Pro Phe Val Glu Asp Ile
65                  70                  75                  80

Val Asp Leu Val Ile Glu Gly Val Lys Val Val Thr Thr Gly Ala
                85                  90                  95

Gly Asn Pro Ser Lys Tyr Met Glu Arg Phe His Glu Ala Gly Ile Ile
            100                 105                 110

Val Ile Pro Val Pro Ser Val Ala Leu Ala Lys Arg Met Glu Lys
            115                 120                 125

Ile Gly Ala Asp Ala Val Ile Ala Glu Gly Met Glu Ala Gly Gly His
    130                 135                 140

Ile Gly Lys Leu Thr Thr Met Thr Leu Val Arg Gln Val Ala Thr Ala
145                 150                 155                 160

Ile Ser Ile Pro Val Ile Ala Ala Gly Gly Ile Ala Asp Gly Glu Gly
                165                 170                 175

Ala Ala Ala Gly Phe Met Leu Gly Ala Glu Ala Val Gln Val Gly Thr
            180                 185                 190

Arg Phe Val Val Ala Lys Glu Ser Asn Ala His Pro Asn Tyr Lys Glu
        195                 200                 205

Lys Ile Leu Lys Ala Arg Asp Ile Asp Thr Thr Ile Ser Ala Gln His
    210                 215                 220

Phe Gly His Ala Val Arg Ala Ile Lys Asn Gln Leu Thr Arg Asp Phe
225                 230                 235                 240

Glu Leu Ala Glu Lys Asp Ala Phe Lys Gln Glu Asp Pro Asp Leu Glu
                245                 250                 255

Ile Phe Glu Gln Met Gly Ala Gly Ala Leu Ala Lys Ala Val Val His
            260                 265                 270

Gly Asp Val Asp Gly Gly Ser Val Met Ala Gly Gln Ile Ala Gly Leu
        275                 280                 285

Val Ser Lys Glu Glu Thr Ala Glu Glu Ile Leu Lys Asp Leu Tyr Tyr
    290                 295                 300

Gly Ala Ala Lys Lys Ile Gln Glu Glu Ala Ser Arg Trp Ala Gly Val
305                 310                 315                 320

Val Arg Asn Asp

```
<210> SEQ ID NO 3
<211> LENGTH: 29
<212> TYPE: DNA
```

```
<213> ORGANISM: Streptococcus pneumoniae

<400> SEQUENCE: 3
aggttggagg ccatatgaaa acgcgtatt                                              29

<210> SEQ ID NO 4
<211> LENGTH: 29
<212> TYPE: DNA
<213> ORGANISM: Streptococcus pneumoniae

<400> SEQUENCE: 4
ggcggatcct tagtcatttc ttacaactc                                              29
```

METHODS OF SCREENING FOR FABK ANTAGONISTS AND AGONISTS

This application claims the benefit of U.S. Provisional Application No. 60/238,366, filed Oct. 6, 2000.

FIELD OF THE INVENTION

This invention relates to methods of using polynucleotides and polypeptides of the Fab family, as well as their variants, herein referred to as "FabK," "FabK polynucleotide(s)," and "FabK polypeptide(s)," as the case may be.

BACKGROUND OF THE INVENTION

Infections caused by or related to bacteria are a major cause of human illness worldwide, and the frequency of resistance to standard antibiotics has risen dramatically over the last decade. Hence, there exists an unmet medical need and demand for new anti-microbial agents against pathogenic bacteria, as well as drug screening methods to identify such agents.

An example of a bacterial enzyme that is resistant to a widely used antibacterial agent, Triclosan, is FabK. This enzyme, involved in fatty acid biosynthesis, has been recently reported from *Streptococcus pneumoniae*, a well-known human pathogen (Heath, et al. *Nature* 406: 145 (2000)). The specific activity of the enzyme under the published conditions was 64+/-4 nmol min$^{-1}$, too low to efficiently screen for compounds that modulate the activity of the enzyme, such as inhibitors (Heath, et al. *Nature* 406: 145 (2000)). The present invention solves this problem by providing a method for screening for FabK agonists and antagonists, wherein FabK activity is sufficient to perform efficient compound screening.

A further problem identified by recent studies has been solved by this invention. Heath teaches that organisms expressing FabK will be refractory to FabI inhibitors, and that bacteria possessing both targets will require a combination of inhibitors to block growth (Heath, et al. *Nature* 406: 145 (2000)). The present invention provides methods of screening for compounds that inhibit both enzymes, as well as the use of such compounds as antimicrobial compounds.

SUMMARY OF THE INVENTION

The present invention relates methods using FabK, in particular FabK polypeptides and FabK polynucleotides, to screen for antimicrobial compounds.

Also provided by the invention is a method of screening for an agonist or antagonist of FabK polypeptide comprising the steps of: providing a reaction mixture comprising a FabK polypeptide; contacting a candidate compound to said reaction mixture; and detecting activation or inhibition of an activity of said FabK polypeptide.

Another aspect of the invention is a method for screening to identify compounds that activate or that inhibit an activity of Fab K polypeptide comprising a method selected from the group consisting of: (a) measuring the binding of a candidate compound to the polypeptide (or to the cells or membranes bearing the polypeptide) or a fusion protein thereof by means of a label directly or indirectly associated with the candidate compound; (b) measuring the binding of a candidate compound to the polypeptide (or to the cells or membranes bearing the polypeptide) or a fusion protein thereof in the presence of a labeled competitor; (c) testing whether the candidate compound results in a signal generated by activation or inhibition of the polypeptide, using detection systems appropriate to the cells or cell membranes bearing the polypeptide; or (d) mixing a candidate conmpound with a solution comprising a FabK polypeptide, to form a mixture, measuring activity of the polypeptide in the mixture, and comparing the activity of the mixture to a standard.

A still further aspect of the invention provides a method wherein said reaction mixture comprises crotonyl ACP and/or an ACP comprising a linked 6 to 8 carbon chain, and/or NADH and/or a cation.

Another aspect of the invention is a method wherein said detecting step comprises measuring a change in light absorption at least 2 time points.

The invention also provides a method wherein FabK polypeptide is an isolated polypeptide selected from the group consisting of: (i) an isolated polypeptide comprising an amino acid having at least 95% identity to the amino acid sequence of SEQ ID NO:2 over the entire length of SEQ ID NO:2; (ii) an isolated polypeptide comprising the amino acid sequence of SEQ ID NO:2, (iii) an isolated polypeptide that is the amino acid sequence of SEQ ID NO:2, and (iv) a polypeptide that is encoded by a recombinant polynucleotide comprising the polynucleotide sequence of SEQ ID NO:1.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to methods using FabK polypeptides and polynucleotides as described in greater detail below. In particular, the invention relates to methods using polypeptides and polynucleotides of a FabK of *Streprococcus pneumoniae*. The invention relates especially to methods using FabK having a nucleotide and amino acid sequences set out in Table 1 as SEQ ID NO:1 and SEQ ID NO:2 respectively. The start codon in SEQ ID NO: 1 begins with nucleotide 1 and the stop codon ends with nucleotide 975. Note that sequences recited in the Sequence Listing below as "DNA" represent an exemplification of the invention, since those of ordinary skill will recognize that such sequences can be usefully employed in. polynucleotides in general, including ribopolynucleotides.

TABLE 1

FabK Polynucleotide and Polypeptide Sequences (A) *Streptococcus pneumoniae*
FabK polynucleotide sequence [SEQ ID NO: 1].

5'-ATGAAAACGCGTATTACAGAATTATTGAAGATTGAcTATCCTATTTTCCAAGGAGGGATGGCC

TGGGTTGCTGATGGTGATTTGGCAGGGGCTGTTTCCAAGGCTGGAGGATTAGGAATTATCGGTGG

TABLE 1-continued

FabK Polynucleotide and Polypeptide Sequences

GGGAAATGCCCCGAAAGAAGTTGTCAAGGCCAATATTGATAAAATCAAATCATTGACTGATAAAC

CCTTTGGGGTCAACATCATGCTCTTATCTCCCTTTGTGGAAGAtATCGTGGATCTCGTTATTGAA

GAAGGTGTTAAAGTTGTCACAACAGGAGCAGGAAATCCAAGCAAGTATATGGAACGTTTCCATGA

AGCTGGGATAATCGTTATTCCTGTTGTTCCTAGTGTCGCTTTAGCTAAACGCATGGAAAAAATCG

GTGCAGACGCTGTTATTGCAGAAGGAATGGAAGCTGGGGGGCATATCGGTAAATTAACAACCATG

ACCTTGGTGCGACAGGTAGCCACAGCTATATCTATTCCTGTTATTGCTGCAGGAGGAATTGCGGA

TGGTGAAGGTGCTGCGGCTGGCTTTATGCTAGGTGCAGAGGCTGTACAGGTGGGGACACGGTTTG

TAGTTGCAAAAGAGTCGAATGCCCATCCAAACTACAAGGAGAAAATTTTAAAAGCAAGGGATATT

GATACTACGATTTCAGCTCAGCACTTTGGTCATGCTGTTCGTGCTATTAAAAATCAGTTGACTAG

AGATTTTGAACTGGCTGAAAAAGATGCCTTTAAGCAGGAAGATCCTGATTTAGAAATCTTTGAAC

AAATGGGAGCAGGTGCCCTAGCCAAAGCAGTTGTTCACGGTGATGTGGATGGTGGCTCTGTCATG

GCAGGTCAAATCGCAGGGCTTGTTTCTAAAGAAGAAACAGCTGAAGAAATCCTAAAAGATTTGTA

TTACGGAGCCGCTAAGAAAATTCAAGAAGAAGCCTCTCGCTGGGCAGGAGTTGTAAGAAATGACT

AA-3'
(B) *Streptococcus pneumoniae* FabK polypeptide
sequence deduced from a polynucleotide sequence in
this table [SEQ ID NO:2].

NH$_2$-

MKTRITELLKIDYPIFQGGMAWVADGDLAGAVSKAGGLGIIGGGNAPKEVVKANIDKIKSLTDKPFGVNIML

LSPFVEDIVDLVIEEGVKVVTTGAGNPSKYMERFHEAGIIVIPVVPSVALAKRMEKIGADAVIAEGMEAGGH

IGKLTTMTLVRQVATAISIPVIAAGGIADGEGAAAGFMLGAEAVQVGTRFVVAKESNAHPNYKEKILKARDI

DTTISAQHFGHAVRAIKNQLTRDFELAEKDAFKQEDPDLEIFEQMGAGALAKAVVHGDVDGGSVMAGQIAGL

VSKEETAEEILKDLYYGAAKKIQEEASRWAGVVRND-COOH

Deposited Materials

A deposit comprising a *Streptococcus pneumoniae* 0100993 strain has been deposited with the National Collections of Industrial and Marine Bacteria Ltd. (herein "NCIMB"), 23 St. Machar Drive, Aberdeen AB2 IRY, Scotland on 11 Apr. 1996 and assigned deposit number 40794. The deposit was described as *Streptococcus pneumoniae* 0100993 on deposit.

On 17 April 1996 a *Streptococcus pneumoniae* 0100993 DNA library in *E. coli* was similarly deposited with the NCUMB and assigned deposit number 40800. The *Streptococcus pneumoniae* strain deposit is referred to herein as "the deposited strain" or as "the DNA of the deposited strain."

The deposited strain comprises a full length FabK gene. The sequence of the polynucleotides comprised in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The deposited strain will be irrevocably and without restriction or condition released to the public upon the issuance of a patent. The deposited strain is provided merely as convenience to those of skill in the art and is not an admission that a deposit is required for enablement, such as that required under 35 U.S.C. §112. A license may be required to make, use or sell the deposited strain, and compounds derived therefrom, and no such license is hereby granted.

In one aspect of the invention there is provided an isolated nucleic acid molecule encoding a mature polypeptide expressible by the *Streptococcus pneumoniae* 0100993 strain, which polypeptide is comprised in the deposited strain. Further provided by the invention are FabK polynucleotide sequences in the deposited strain, such as DNA and RNA, and amino acid sequences encoded thereby. Also provided by the invention are FabK polypeptide and polynucleotide sequences isolated from the deposited strain.

Polypeptides

FabK polypeptide of the invention is substantially phylogenetically related to other FabK polypeptides from other species.

In one aspect of the invention there are methods provided using polypeptides of *Streptococcus pneumoniae* referred to herein as "FabK" and "FabK polypeptides" as well as biologically, therapeutically or clinically useful variants thereof, and compositions comprising the same, useful in such methods.

Among the particularly preferred embodiments of the invention are methods using variants of FabK polypeptide encoded by naturally occurring alleles of a FabK gene, particularly in candidate compound screening.

The present invention further provides methods using an isolated polypeptide that: (a) comprises or consists of an amino acid sequence that has at least 95% identity, most preferably at least 97–99% or exact identity, to that of SEQ ID NO:2 over the entire length of SEQ ID NO:2; (b) a polypeptide encoded by an isolated polynucleotide comprising or consisting of a polynucleotide sequence that has at least 95% identity, even more preferably at least 97–99% or exact identity to SEQ ID NO:1 over the entire length of SEQ ID NO: 1; (c) a polypeptide encoded by an isolated polynucleotide comprising or consisting of a polynucleotide sequence encoding a polypeptide that has at least 95% identity, even more preferably at least 97–99% or exact identity, to the amino acid sequence of SEQ ID NO:2, over the entire length of SEQ ID NO:2.

The polypeptides of the methods of the invention include, for example, a polypeptide of Table 1 [SEQ ID NO:2] (in particular a mature polypeptide) as well as polypeptides and fragments, particularly those that has a biological activity of FabK, and also those that have at least 95% identity to a polypeptide of Table 1 [SEQ ID NO:2] and also include portions of such polypeptides with such portion of the polypeptide generally comprising at least 30 amino acids and more preferably at least 50 amino acids, particularly those portions possessing an activity of a wild type FabK.

The invention also includes methods using a polypeptide consisting of or comprising a polypeptide of the formula:

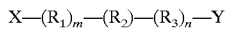

wherein, at the amino terminus, X is hydrogen, a metal or any other moiety described herein for modified polypeptides, and at the carboxyl terminus, Y is hydrogen, a metal or any other moiety described herein for modified polypeptides, $R_1$ and $R_3$ are any amino acid residue or modified amino acid residue, m is an integer between 1 and 1000 or zero, n is an integer between 1 and 1000 or zero, and $R_2$ is an amino acid sequence of the invention, particularly an amino acid sequence selected from Table 1 or modified forms thereof. In the formula above, $R_2$ is oriented so that its amino terminal amino acid residue is at the left, covalently bound to $R_1$, and its carboxy terminal amino acid residue is at the right, covalently bound to $R_3$. Any stretch of amino acid residues denoted by either $R_1$ or $R_3$, where m and/or n is greater than 1, may be either a heteropolyter or a homopolymer, preferably a heteropolymer. Other preferred embodiments of the invention are provided where m is an integer between 1 and 50, 100 or 500, and n is an integer between 1 and 50, 100, or 500.

It is most preferred in the methods of the invention that the polypeptide used is derived from *Streptococcus pneumoniae*; however, it may also be obtained from other organisms of the same taxonomnic genus. Methods are also provided using polypeptides from organisms of the same taxonomic family or order, among other organisms as described elsewhere herein.

For the purposes of this invention, a fragment is a variant polypeptide having an amino acid sequence that is entirely the same as part but not all of any amino acid sequence of any polypeptide used in the methods of the invention. As with FabK polypeptides, fragments may be "free-standing," or comprised within a larger polypeptide of which they form a part or region, most preferably as a single continuous region in a single larger polypeptide.

Preferred fragments used in the methods of the invention include, for example, truncation polypeptides having a portion of an anino acid sequence of Table 1 [SEQ ID NO:2], or of variants thereof, such as a continuous series of residues that includes an amino- and/or carboxyl-terminal amino acid sequence, particularly those possessing an enzymatic function of wild type FabK.

Antagonists and Agonists—Assays and Molecules

Polypeptides and polynucleotides described herein may be used to assess the binding or other effects of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

Polypeptides and polynucleotides described herein are responsible for many biological functions, including many disease states, in particular the Diseases herein mentioned, among others. In view of this, the present invention provides for a method of screening candidate compounds to identify those that agonize (e.g., stimulate) or that antagonize (e.g., inhibit) a function of a polypeptide or polynucleotide of the invention, as well as related polypeptides and polynucleotides. In general, agonists or antagonists may be employed for therapeutic and prophylactic purposes against such Diseases as herein mentioned. Compounds (herein also "candidate compound(s)") may be identified or selected from a variety of sources, for example, cells, cell-free preparations, known or newly synthesized compounds, chemical libraries, and natural product rnixtures. Such compounds, such as agonists and antagonists, so-identified may be natural or modified substrates, ligands, receptors, enzymes, etc., as the case may be, of FabK polypeptides and polynucleotides; or may be structural or functional mirnetics thereof (see Coligan et al., *Current Protocols in Immunology* 1(2):Chapter 5 (1991)).

Antagonists of the invention include, among others, small organic molecules, peptides, polypeptides and antibodies that bind to a polynucleotide and/or polypeptide of the invention and thereby inhibit or extinguish its activity or expression. Antagonists also may be a small organic molecule, a peptide, a polypeptide, a closely related protein or antibody that binds the same sites on a binding molecule without inducing FabK-induced activities. Such antagonists preferably prevent the action or expression of FabK polypeptides and/or polynucleotides by excluding FabK polypeptides andlor polynucleotides from binding.

Other antagonists or agonists of the invention include compounds that alter the binding of a cation to FabK, or alter an activity of a cation on FabK, particularly a monovalent cation. It is preferred that such antagonists inhibit such binding or lower such activity.

Preferred agonists and antagonists of the invention are those that also agonize or antagonize an activity of FabI. An agonist of FabI may act as an antagonist of FabK and visa versa, or such compounds may agonize or antagonize both FabI and FabK. The invention provides that these agonists and antagonists, when used as antimicrobial compounds, will be less likely to generate resistant mutants than for compounds that only act on a single target. This is a significant and surprising discovery in view of the teachings of Heath indicating that organisms that express FabK will be refractory to FabI inhibitors, and that bacteria possessing both targets will require a combination of inhibitors to block growth (Heath, et al. *Nature* 406: 145 (2000))

Antagonists of the invention further include small molecules that bind to and occupy the binding site of a FabK polypeptide thereby preventing binding to cellular binding molecules, such that normal biological activity is prevented. Examples of small molecules include but are not limited to small organic molecules, peptides or peptide-like molecules. Other antagonists include antisense molecules (see Okano, J. Neurochem. 56: 560 (1991); OUGODEOXYNUCLEOTIDES AS ANTISENSE INHIBITORS OF GENE EXPRESSION, CRC Press, Boca Raton, Fla. (1988), for a description of these molecules).

Candidate compounds of the invention that are small molecules preferably have a molecular weight below 2,000 daltons, more preferably between 300 and 1,000 daltons, and most preferably between 400 and 700 daltons. It is particularly preferred that these small molecules are organic molecules.

The screening methods of the invention may simply measure the binding of a candidate compound to a FabK polypeptide or polynucleotide, or to cells or membranes bearing a FabK polypeptide or polynucleotide, or a fusion protein of a FabK polypeptide by means of a label directly or indirectly associated with a candidate compound. Alternatively, the screening method may involve competition with a labeled competitor. Further, these screening methods may test whether a candidate compound results in a signal generated by activation or inhibition of a FabK polypeptide or polynucleotide, using detection systems appropriate to the cells comprising a FabK polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists, in the absence of an agonist or antagonist, by testing whether the candidate compound results in inhibition of activation of the polypeptide or polynucleotide, as the case may be. Further, the screening methods may simply comprise the steps of mixing a candidate compound with a solution comprising a polypeptide or polynucleotide of the present invention, to form a mixture, measuring FabK polypeptide and/or polynucleotide activity in the mixture, and comparing the FabK polypeptide and/or polynucleotide activity of the mixture to a standard. Fusion proteins, such as those made from Fc portion and FabK polypeptide, as herein described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., J Biol Chem, 270(16):9459–9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents that may inhibit or enhance the production of polypeptide (also called antagonist or agonist, respectively) from suitably manipulated cells or tissues.

The invention also provides a method of screening candidate compounds to identify those that stimulate or inhibit an activity of FabK polypeptides or polynucleotides, particularly those compounds that are bacteristatic and/or bactericidal. The method of screening may involve high-throughput techniques. For example, to screen for agonists or antagonists, a synthetic reaction mix, a cellular compartrent, such as a membrane, cell envelope or cell wall, or a preparation of any thereof, comprising FabK polypeptide and a labeled substrate or ligand of such polypeptide is incubated in the absence or the presence of a candidate molecule that may be a FabK agonist or antagonist. The ability of a candidate molecule to agonize or antagonize the FabK polypeptide is reflected in decreased binding of the labeled ligand or decreased production of product from such substrate. Molecules that bind gratuitously, i.e., without inducing the effects of FabK polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to calorimetric, labeled substrate converted into product, a reporter gene that is responsive to changes in FabK polynucleotide or polypeptide activity, and binding assays known in the art.

Polypeptides of the invention may be used to identify membrane bound or soluble receptors, if any, for such polypeptide, through standard receptor binding techniques known in the art. These techniques include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (e.g., cells, cell membranes, cell supernatants, tissue extracts, bodily materials). Other methods include biophysical techniques such as surface plasmon resonance and spectroscopy. These screening methods may also be used to identify agonists and antagonists of the polypeptide that compete with the binding of the polypeptide to its receptor(s), if any. Standard methods for conducting such assays are well understood in the art.

The fluorescence polarization value for a fluorescently-tagged molecule depends on the rotational correlation time or tumbling rate. Protein complexes, such as formed by FabK polypeptide associating with a candidate compound, labeled to comprise a fluorescently-labeled molecule will have higher polarization values than a fluorescently labeled FabK protein not bound to a candidate compound. It is preferred that this method be used to characterize small molecules that bind FabK.

Surface plasmon resonance can be used to monitor the effect of small molecules on FabK polypeptide self-association as well as an association of FabK polypeptide and another polypeptide or small molecule. FabK polypeptide can be coupled to a sensor chip at low site density such that covalently bound molecules will be monomeric. Solution protein can then passed over the FabK polypeptide-coated surface and specific binding can be detected in real-time by monitoring the change in resonance angle caused by a change in local refractive index. This technique can be used to characterize the effect of small molecules on kinetic rates and equilibrium binding constants for FabK polypeptide self-association as well as an association of FabK polypeptide and another polypeptide or small molecule.

In other embodiments of the invention there are provided methods for identifying compounds that bind to or otherwise interact with and inhibit or activate an activity or expression of a FabK polypeptide and/or polynucleotide of the invention comprising: contacting a FabK polypeptide and/or polynucleotide of the invention with a compound to be screened under conditions to permit binding to or other interaction between the compound and the FabK polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the FabK polypeptide and/or polynucleotide by detecting the presence or absence of a signal generated from the binding or interaction of the compound with the FabK polypeptide and/or polynucleotide.

Another example of an assay for FabK agonists or antagonists is a competitive assay that combines FabK and a potential agonist or antagonist with FabK-binding molecules, recombinant FabK binding molecules, natural substrates or ligands, or substrate or ligand mimetics, under appropriate conditions for a competitive inhibition assay. FabK can be labeled, such as by radioactivity or a colorimetric compound, such that the number of FabK molecules bound to a binding molecule or converted to product can be determined accurately to assess the effectiveness of the potential agonist antagonist.

A further assay is provided whereby compounds that are agonists or antagonists of FabK are assayed to determine whether they are also agonists or antagonists of FabI, and visa versa. Embodiments are also provided where an assay mixture comprises both FabI and FabK.

FabK catalyses the reduction of enoyl-ACPs with the concomitant oxidation of NADH. Screening methods based on this reaction are preferred embodiments herein. Such methods may comprise the step of detecting reduction of crotonoyl-ACP to butyryl-ACP. Detection may be monitored, for example, by following the change in absorbance at a particular wavelength in the light spectrum, preferably at 340 nm, or by any other means of assaying NADH oxidation. Assays may be carried out, for example, in Costar 3696 half-area plates, preferably at a final assay volume of 150 ul on a Spectramax platereader. Preferred substrates used in the methods of the invention are NADH, NADPH, an NADH analogue, crotonoyl ACP, crotonyl CoA, and ACP comprising crotonyl analogues or homologues, such as compounds having longer carbon chains, particularly from 6 to 8 carbons, among others. Further provided are preferred methods comprising the step of incubating substrates with FabK enzyme in 100 mM N-[2-acetamido]-2 iminodiacetic acid (ADA), pH 6.5, 100 mM $NH_4Cl$, 4% glycerol at 30° C., followed by an incubation step for 30 minutes after the addition of FabK. This reaction may be monitored at 340 nm, among other wavelengths.

A particularly preferred embodiment is a method comprising the step of providing monovalent cations to an assay mnixture. This step enhances the activity of FabK enzyre. Any cation, or any compound that increases or enhances the activity of the enzyme, may be used in this method; however, $NH_4^+$ is preferred, and a concentration of 100 mM is most-preferred. Adding cations to the assay mixture is vastly superior to assaying in the absence of added cation. The activation in the reaction may be about 300-fold over the reaction with no monovalent cations added, such as in a cell-lysate assay without additional cations.

Using the assay methods of the invention, compounds may be tested for inhibition of FabK. It is preferred that the assay is performed using an assay volume of between 5 and 200 ul of candidate compound, more preferably 10 and 50 ul of candidate compound, and most preferably 30 ul, Preferred methods also utilize NADH, crotonoyl ACP and crotonyl CoA in the assay mixture. In preferred embodiments of the methods of the invention, the final concentration in the assay mixture is between 10 uM and 50 uM crotonoyl ACP, but is most preferably 25 uM crotonoyl ACP; is between 20 uM and 100 uM NADH, but is most preferably 50 uM NADH; and is between 0.25 nM and 1.75 nM FabK enzyme, but is most preferably 1.25 nM FabK enzyme.

It is preferred that the assay mixtures are incubated at between 20° C. and 40° C., preferably between 28° C. to 37° C., and most preferably at about 30° C. Preferred incubation times range between 30 seconds and 1 hour, are more preferably between 3 minutes and 30 minutes, and are most preferably about 4 or 5 minutes.

In certain preferred embodiments positive controls, without added candidate compound, are used in a reaction well to gauge the degree of agonism or antagonism of a candidate compound. Negative controls, without enzyme, may also be used.

Glossary

The following definitions are provided to facilitate understanding of certain terms used frequently herein.

"Disease(s)" means any disease caused by or related to infection by a bacteria, including, for example, otitis media, conjunctivitis, pneumonia, bacteremia, meningitis, sinusitis, pleural empyema and endocarditis, and most particularly meningitis, such as for example infection of cerebrospinal fluid.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994, *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM J. *Applied Math.*, 48: 1073 (1988). Methods to determine identity are designed to give the largest match between the sequences tested. Moreover, methods to determine identity are codified in publicly available computer programns. Computer program methods to determine identity between two sequences include, but are not limited to, the GCG program package (Devereux, J., et al., *Nucleic Acids Research* 12(1): 387 (1 984)), BLASTP, BLASTN, and FASTA (Altschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following: Algorithm: Needleman and Wunsch, 1: Mol Biol. 48: 443–453 (1970)

Comparison matrix: BLOSSUM62 from Hentikoff and Hentikoff, Proc. Natl. Acad. Sci. USA. 89:10915–10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch, J. Mol Biol. 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n \cdot (x_n \cdot y),$$

wherein $n_n$ is the number of nucleotide alterations, $x_n$ is the total number of nucleotides in SEQ ID NO:1, y is 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

(2) Polypeptide embodiments further include an isolated polypeptide comprising a polypeptide having at least a 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected fromthe group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a \cdot (x_a \cdot y),$$

wherein $n_a$ is the number of amino acid alterations, $x_a$ is the total number of amino acids in SEQ ID NO:2, y is 0.95 for 95%, 0.97 for 97% or 1.00 for 100%, and · is the symbol for the multiplication operator, and wherein aiyy non-integer product of $x_a$ and y is rounded down to the nearest integer prior to subtracting it from $x_a$.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Organism(s)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxelia, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillur, Campylobacter, Shigella, Legionella, Pseudomonas, Aeromonas, Rickettsia, Chiamydia, Borrelia and Mycoplasma, and further including, but not limited to, a member of the species or group, Group A Streptococcus, Group B Streptococcus, Group C Streptococcus, Group D Streptococcus, Group G Streptococcus, Streptococcus pneumoniae, Streptococcus pyogenes, Streptococcus agalactiae, Streptococcus faecalis, Streptococcus faecium. Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israeli, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophiius ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flewneri, Pseudomonas aeruginosa, Franscisella tularensis, Brucella abortis, Bacillus anthracis, Bacillus cereus, Clostridium perfringens, Clostridiun tetani, Clostridium boiulinum, Treponema pallidum Rickettsia rickettsii, Helicobacter pylori and Chiamydia trachomitis, (ii) an archaeon, including but not limited to Archaebacter, and (iii) a unicellular or filamentous eukaryote, including but not limited to, a protozoan, a fungus, a member of the genus Saccharomyces, Kluveromyces, or Candida, and a member of the species *Saccharomyces ceriviseae, Kluveromyces lactis,* or *Candida albicans.*

"Polynucleotide(s)" generally refers to any polyribonucleotide or polydeoxyribonucleotide, that may be unmodified RNA or DNA or modified RNA or DNA. "Polynucleotide(s)" include, without limitation, single- and double-stranded DNA, DNA that is a mixture of single- and stranded regions or single-, double- and triple-siranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions nay be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that comprise he one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the terrn is used herein. It will be appreciated that a great variety of modifications have been made to DNA and RNA that serve many useful purposes known to those of skill in the art. The term "polynucleotide (s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl tenini. Modifications include, for example, acetylation, acylation, ADP-ribosylation, amidation, covalent attachrnent of flavin, covalent attachment of a herne moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutarnate, formylation, gannn-carboxylationI; GPI anchor formation, hydroxylation, iodination, methylation, myristoylation, oxidation, proteolytic processing, phosphorylation, prenylation, racemization, glycosylation, lipid attachment, sulfation, gamma-carboxylation of glutarnic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., *Meth. Enzymol.* 182:626–646 (1990) and Rattan et al., *Protein Synthesis: Posttranslationaf Modifications and Aging,* Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Recombinant expression system(s)" refers to expression systems or portions thereof or polynucleotides of the invention introduced or transformed into a host cell or host cell lysate for the production of the polynucleotides and polypeptides of the invention.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ble; among Ser and Thr; among the acidic residues Asp and Glu; among Asn and Gin; and among the basic residues Lys and Arg; or aromatic residues Phe and Tyr. Particularly preferred are variants in which several, 5–10, 1–5, 1–3, 1–2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, that are well known and routine to those of skill

Example 1

Cloning of *Streptococcus pneumoniae* FabK

The *S.pneumoniae* fabK, enoyl-ACP reductase gene was PCR amplified from *S.pneumoniae* strain 0100993. The forward and reverse primer sequences were 5'AGGTTGGAGGCCATATGAAAACGCGTATT3' (SEQ ID NO:3) and 5'GGCGGATCCTTAGTCATTTCTTACAACTC3' (SEQ ID NO:4), respectively. An NdeI site was integrated into the forward primer and a BamHl site into the reverse primer for cloning into pET24b(+). The PCR product was digested with the restriction endonucleases NdeI and BamHl and then ligated into pET24b(+), (also digested with NdeI and BamHl). The resulting plasmid was transformed into subcloning efficiency DH5-alpha cells. The sequence of the pET24bSpfabK expression construct was confirmed by DNA sequencing and the plasmid was transformed into electrocompetent BL21 (DE3) cells harboring the tRNA vector pRR692.

Intact FabK is expressed as 25% total cell protein of which 80% is soluble when induced with 0.1 mM IPTG at 37° C. for three hours.

Example 2

Purification of *S.pneumoniae* FabK

One liter of cells containing the FabK expression construct were grown to an OD600 of 0.6. Expression was induced with 0.1 mM IPTG and the cells were grown for a further 3 h and then harvested. The cell pellet was resuspended in 10 ml 50 mM Tris pH7.5, 1 mM PMSF, 1 mM Benzatidine, 1 mM DTT (buffer A) and lysed by sonication. Cell debris was removed by centrifugation. The supernatant was loaded onto a Hi-load Q (16/10) column (Pharmacia) equilibrated in buffer A. Protein was eluted over a 200 ml gradient of 0–100% buffer B, where buffer B is buffer A+1 M KCl. Fractions containing FabK wereidentified by their absorbance at A460 and by their FabK activity and pooled.

1.5 M ammonium sulphate was added to the pooled fractions and these were then loaded onto a Hi-load Phenyl sepharose (16/10) column (Pharmacia) equilibrated in 50 mM Tris pH 7.5, 1 mM PMSF, 1 mM Benzamidine, 1 mM DTT, 1.5 M ammonium sulphate. Proteins were eluted with a gradient of ammonium sulphate (1.5 to 0 M) over 200 ml. Fractions containing FabK were identified as above and pooled. The pooled fractions were buffer exchanged into 100 mM Tris, pH 7.5, 2 mM DTT and glycerol was then added to 50%. The protein was stored at −20° C. It is preferred that the enzyme be stored with $NH_4Cl$, which has been found to stabilize the enzyme.

The amino acid sequence of FabK in the Examples is:

MKTRITELLKIDYPIFQGGMAWVADGDLAG-
AVSKAGOLGIIGGGNAPKEVVKANIDKI KSLTD-
KPFGVNIMLLSPFVEDIVDLVIEEGVKV-
VTTGAGNPSKYMERFHEAGIIVUVVP SVA-
LAKRMEKIGADAVIAEGMEAGGHIGKLTT-
MTLVRQVATAISIPVIAAGGIADGEGA AAG-
FMLGAEAVQVGTRFVVAKESNAHPNYKEKIL-
KARDIDTTISAQHFGHAVRAIKNQ LTRDFE-
LAEKDAFKQEDPDLEBFEQMGAGALAKAV-
VHGDVDGGSVMAGQIAGLVSKE ETAEEILKD-
LYYGAAKKIQEEASRWAGVVRND (SEQ ID NO:2)

Example 3

FabK Characterization

The identity of the protein was confirmed by N-terminal sequencing and MALDI mass spectrometry. The optical spectrum of the protein was characteristic of flavoproteins, showing an absorbance in the 450nm region. The FAD cofactor was removed by denaturation of the protein and quantified. The ratio of FAD:protein was shown to be approximately 1:1.

Example 4

Assaying the Activity of FabK

FabK catalyses the reduction of enoyl-ACPs with the concommitant oxidation of NADH. Crotonoyl-ACP can be prepared as described below. The reduction of crotonoyl-ACP to butyryl-ACP can be monitored by following the change in absorbance at 340 nm as NADH is oxidised.

Assays were carried out in Costar 3696 half-area plates in a final assay volume of 150 ul on a Spectramax platereader. Substrates, NADH and crotonoyl ACP, were incubated with FabK enzyme in 100 mM N-[2-acetamido]-2 iminodiacetic acid (ADA), pH 6.5, 100 mM $NH_4Cl$, 4% glycerol at 30° C. and the reaction monitored at 340 nm. This assaying can also be performed using crotonyl CoA, NADPH or an NADH analogue as a substrate.

Example 5

Activation by Monovalent Cations

FabK was found to be activated by monovalent cations. The greatest activation was found to be with $NH_4^+$ at 100 mM, which activated the reaction about 300 fold over the reaction with no monovalent cations.

Example 6

Compound Screening

Using the above assay, compounds can be tested for inhibition of FabK. 30 ul of a candidate compounds is added to a well of the plate. 30 ul of a 250 uM stock of NADH is then added to the well. 60 ul of a 67.5 uM stock of Crotonoyl ACP is added to the well. The plate is incubated at 30° C. for 5 min. 30 ul of a 6.25 nM stock of enzyme is then added to the well (also preincubated at 30° C.) to initiate the reaction. The plate is then monitored at A340 nm for 30 min at 30° C. Positive controls are reactions without compound. Negative controls are reactions without enzyme and without compound. Final concentrations in the assay mixture are 25 uM crotonoyl ACP, 50 uM NADH, 1.25 nM enzyme.

Example 7

Synthesis of Crotonoyl-ACP

Crotonoyl-ACP was synthesised using *S. pneumoniae* ACP synthase to catalyse the addition of a crotonoyl group from crotonoyl CoA to *E.coli* apo-acyl carrier protein (ACP).

To a reaction vessel containing 500 mg (58 μmol) of *E. coli* apo-ACP in 20 mM Bis-Tris, pH 6.8, 5 mM $MgCl_2$, was added 76 mg (81 μmoles) of crotonoyl-CoA and 5 mg of *S.*

*pneunioniae* ACP synthase. The final volume and pH were adjusted to 100 mL and 6.8, respectively. The pH of the reaction was maintained at 6.8 with NaOH and monitored for completion by mass spectrometry. Conversion was complete within 150 min with no detectable by-products. The reaction mixture was loaded at 10 mLnlmin onto a Q-Sepharose FF column (5×16 cm) pre-equilibrated with 20 mM Bis-Tris, pH 6.8. Crotonoyl-ACP was eluted over 2200 ml using a 0.2M–0.6M NaCl gradient at a flow rate of 20 ml/min. Fractions were monitored by mass spectrometry for identity and purity. The appropriate fractions were pooled and concentrated using a YM-3 membrane.

Example 8

FabI Assay Method

FabI enzyme, and methods of making and using it, is disclosed in patent applications numbered PCT/US00/12104 and EP1997000306506.

FabI catalyses the reduction of enoyl-ACPs with the concomitant oxidation of NAD(P)H. Crotonoyl-ACP can be prepared as described in patent applications numbered PCT/US00/12104 and EP1997000306506. The reduction of enoyl-ACPs can be monitored by following the change in absorbance at 340 nm as NADH is oxidised. Enoyl ACPs (e.g. crotonoyl-ACP) can be replaced by enoyl-CoAs (e.g. crotonoyl-CoA)

Assays were carried out in Costar 3696 half-area plates in a final assay volume of 150 μl on a Spectramax platereader. Substrates, NADH and crotonoyl ACP, were incubated with FabI enzyme in 100 mM N-[2-acetamido]-2 iminodiacetic acid (ADA), pH 6.5, 4% glycerol at 30° C. and the reaction monitored at 340 nm. This assaying can also be performed using crotonyl CoA, NADPH or an NADH analogue as a substrate, or using a substrate suitable for FabK, such as those described above.

Using the above assay, compounds can be tested for inhibition of FabI. 30 μl of a candidate compounds is added to a well of the plate. 30 μl of a 250 μM stock of NADH is then added to the well. 60 μl of a 67.5 μM stock of Crotonoyl ACP is added to the well. The plate is incubated at 30° C. for 5 minutes. 30 μl of a 6.25 nM stock of enzyme is then added to the well (also preincubated at 30° C.) to initiate the reaction. The plate is then monitored at A340nm for 30 minutes at 30° C. Positive controls are reactions without compound. Negative controls are reactions without enzyme and without compound. Final concentrations in the assay mixture are 25 μM crotonoyl ACP and 50 μM NADH.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

What is claimed is:

1. A method of screening for an agonist or antagonist of a FabK polypeptide comprising:
   contacting an isolated FabK polypeptide comprises SEQ ID NO: 2 with a candidate compound in the presence of an $NH_4$ cation; and
   detecting activation or inhibition of an activity of said FabK polypeptide wherein said FabK polypeptide comprises SEQ ID NO: 2 and has enhanced activity in the presence of $NH_4^+$.

2. The method of claim 1 wherein said contacting is carried out in the presence of enoyl-ACP.

3. The method of claim 2 wherein said contacting is carried out in the presence of NADH.

4. The method of claims 1 wherein said detecting step comprises measuring a change in light absorption at least 2 time points.

5. The method of claim 1 wherein FabK polypeptide is an isolated polypeptide that is encoded by a recombinant polynucleotide comprising the polynucleotide sequence of SEQ ID NO:1.

6. The method of claim 1 wherein said contacting is carried out in the presence of NADPH.

7. The method of claim 1, wherein said detecting step comprises measuring the rate of reduction of enoyl-ACP.

8. The method of claim 7, wherein the enoyl-ACP is crotonoyl-ACP.

9. The method of claim 1, wherein said detecting step comprises assaying the concentration of NADH.

10. The method of claim 9, wherein the step of assaying the concentration of NADH comprises measuring absorbance at about 340 nm.

11. The method of claim 2, wherein the enoyl-ACP is crotonoyl-ACP.

12. The method of claim 1, wherein said $NH_4$ cation is at a concentration of at least about 100 mM.

* * * * *